(12) United States Patent
Kotchapaw

(10) Patent No.: US 10,206,803 B2
(45) Date of Patent: Feb. 19, 2019

(54) TOOL SUPPORTING WRIST BRACE

(71) Applicant: Landon Kotchapaw, Toronto (CA)

(72) Inventor: Landon Kotchapaw, Toronto (CA)

( * ) Notice: Subject to any disclaimer, the term of this patent is extended or adjusted under 35 U.S.C. 154(b) by 0 days.

(21) Appl. No.: 15/743,524

(22) PCT Filed: Jul. 13, 2016

(86) PCT No.: PCT/CA2016/050826
§ 371 (c)(1),
(2) Date: Jan. 10, 2018

(87) PCT Pub. No.: WO2017/008162
PCT Pub. Date: Jan. 19, 2017

(65) Prior Publication Data
US 2018/0200097 A1   Jul. 19, 2018

Related U.S. Application Data

(60) Provisional application No. 62/191,604, filed on Jul. 13, 2015.

(51) Int. Cl.
| | |
|---|---|
| *B25G 1/10* | (2006.01) |
| *A61F 5/00* | (2006.01) |
| *A61F 5/01* | (2006.01) |

(52) U.S. Cl.
CPC ............. *A61F 5/0118* (2013.01); *B25G 1/102* (2013.01)

(58) Field of Classification Search
CPC .... A01B 1/026; A61F 5/0118; A61F 5/05866; B25G 1/01; B25G 1/102

USPC .................. 294/25, 58, 59; 16/430
See application file for complete search history.

(56) References Cited

U.S. PATENT DOCUMENTS

| | | | | |
|---|---|---|---|---|
| 1,061,014 | A * | 5/1913 | Sawyer ................ | A61F 13/105 119/633 |
| 3,541,990 | A * | 11/1970 | Du Mas ................ | B63B 35/817 104/202 |
| 4,011,596 | A | 3/1977 | Chang | |
| 4,684,122 | A * | 8/1987 | Desmond ............... | A63B 71/00 482/105 |
| 5,415,623 | A * | 5/1995 | Cherubini .............. | A43B 7/141 264/222 |
| 5,471,698 | A * | 12/1995 | Francis .................. | A47L 13/08 15/144.1 |
| 5,652,955 | A | 8/1997 | Skewis | |
| 5,672,150 | A | 9/1997 | Cox | |
| 5,716,087 | A * | 2/1998 | Backich ................. | A01B 1/02 16/422 |
| 5,846,168 | A * | 12/1998 | Murray ............... | A63B 21/4019 482/105 |

(Continued)

*Primary Examiner* — Dean J Kramer

(74) *Attorney, Agent, or Firm* — Ryan W. Dupuis; Ade + Company Inc.; Kyle R. Satterthwaite

(57) ABSTRACT

A wrist brace device has a splint member including an arm portion for support along an inner forearm of a user, and a palm portion for supporting a palm on a palm supporting surface of the palm portion which is oriented generally in the direction of the arm portion to prevent overextension of the hand of the user relative to the forearm. A tool receiving surface is provided on the palm portion opposite from the palm supporting surface for engaging a handle of a tool thereon such that impacts from a tool head of the tool are directed substantially perpendicularly to the upper palm supporting surface and the arm portion of the user.

19 Claims, 4 Drawing Sheets

(56) References Cited

U.S. PATENT DOCUMENTS

| | | | | |
|---|---|---|---|---|
| 6,328,706 | B1 | 12/2001 | Yattavong | |
| 6,394,516 | B1 * | 5/2002 | Zhuravsky | A47G 21/08 |
| | | | | 224/218 |
| 7,124,536 | B2 * | 10/2006 | Harkey | A01K 87/08 |
| | | | | 43/21.2 |
| 7,837,641 | B2 | 11/2010 | Hoffman | |
| 8,267,844 | B2 * | 9/2012 | Kassel | A63B 21/4021 |
| | | | | 482/139 |
| 2006/0174449 | A1 * | 8/2006 | Hughes | A61F 4/00 |
| | | | | 16/430 |

* cited by examiner

TOOL SUPPORTING WRIST BRACE

FIELD OF THE INVENTION

The present invention relates to a wrist brace for extending along an inner forearm and the palm of the user and which further includes a tool receiving surface thereon configured for engaging a tool handle, for example a D-shaped closed loop shovel handle, such that impacts from use of the tool are distributed over a larger area of the wrist and forearm of the user while the wrist is maintained in a neutral ergonomic position in which the palm of the user is substantially coplanar with the inner forearm of the user.

BACKGROUND

Canada holds more than 10% of the world's standing forests and is the world's leading exporter of timber products. Timber companies that extract resources are legally required to replenish the land from which they extract their timber (standing trees). Each year over 400,000 hectares of land are replenished by seasonal tree planting workers who plant each individual tree by hand.

The task of tree planting is extremely difficult and can be very damaging to the body. Common types of injuries amongst tree planters include hand, wrist and forearm injuries. These injuries are a direct result from the high impact force that results from a tree planter thrusting a tree-planting shovel into the earth. The force of impact which results from thrusting a shovel into the earth is extremely damaging to the body. The majority of the impact is absorbed by the users palm of the hand and wrist. This motion which can occur between 1500 and 4000 times per day can cause some serious problems for the worker and often forces workers to take days off to heal and even leave the profession due to such serious injury.

The repetitive task of tree planting results in several injuries for the workforce employed. Research suggests that 90% of tree planters will sustain some form of a work related injury over the course of their career, as reported in Smith, T. J. (1987). Occupational characteristics of tree planting work. *Silviculture Magazine,* 2 12-17.

As reported in Cobb, T. K., An, K.-N., & Cooney, W. P. (1995), Externally applied forces to the palm increase carpal tunnel pressure, *The Journal of Hand Surgery,* 20A(2), 181-185, given that high repetition-high force occupations involving use of the hand are strongly associated with carpal tunnel syndrome (CTS), it is not surprising that tree planters often report hand, wrist and forearm pain. Wrist pain is one of the most commonly reported complaints among tree planters and has become a large contributor to lost worktime in the tree planting industry as reported in Denbeigh, K., Slot, T. R., & Dumas, G. A. (2013), Wrist postures and forces in tree planters during three tree unloading conditions, *Ergonomics,* 56(10) 1599-1607.

The overextension of the wrist is a highly common occurrence amongst tree planters and can cause a variety of injuries.

Various examples of prior art wrist supporting devices are disclosed in U.S. Pat. No. 7,837,641 by Hoffman, U.S. Pat. No. 5,716,087 by Backich et al, U.S. Pat. No. 5,437,620 by Shelly, and U.S. Pat. No. 5,313,735 by Latouche.

Wrist braces currently on the market are either not suited for use with shovel handle, or when intended for supporting a tool are not strong enough to hold the wrist in the proper neutral position.

Extensive searching in the market place has failed to locate a product that would address the issues discussed.

SUMMARY OF THE INVENTION

The present invention seeks to provide a wrist brace device that is able to support the wrist in a substantially neutral position by preventing overextension, while providing an absorptive surface to reduce impact of the shovel grip on the palm of the hand. The present invention also independently seeks to provide a holding mechanism so that tree planters do not have to grip the shovel for extensive periods of time. The wrist brace device provides support to the wrist while also providing other useful benefits as described herein.

According to one aspect of the invention there is provided a wrist brace device comprising:

a splint member including an arm portion and a palm portion which are rigid and fixed relative to one another;

the arm portion having an arm supporting surface extending in a longitudinal direction for extending longitudinally along a portion of an inner forearm of a user for securement in relation to the inner forearm of the user;

the palm portion having an upper palm supporting surface and a lower tool receiving surface opposite from the upper palm supporting surface;

the upper palm supporting surface extending from the arm portion in the longitudinal direction of the arm portion such that the palm portion is configured to support a palm of the user thereon to extend in a direction of the inner forearm of the user; and the lower tool receiving surface being configured to receive a tool handle thereon substantially in alignment with the palm of the user.

According to a second aspect of the present invention there is provided a method of supporting a work tool comprising a shaft extending in a longitudinal direction between a first end and a second end, a handle supported perpendicularly to the shaft at the first end of the shaft, and a tool head supported on the shaft at the second end of the shaft which is configured for being impacted in the longitudinal direction of the shaft, wherein the method comprises:

providing a splint member including i) an arm portion, ii) a palm portion that is rigid and fixed relative to the arm portion which has an upper palm supporting surface extending from the arm portion in the longitudinal direction of the arm portion, and iii) a lower tool receiving surface opposite from the upper palm supporting surface;

supporting the rigid splint member such that the arm portion extends longitudinally along a portion of an inner forearm of a user and such that the palm portion supports a palm of the user thereon to extend in the longitudinal direction of the arm portion that extends along the inner forearm of the user; and engaging the handle against the lower tool receiving surface such that impacts from the tool head are directed substantially perpendicularly to the upper palm supporting surface and the palm of the user supported thereon.

In addition to various advantages outlined in the following, the present invention i) provides an absorptive surface to reduce the impact of the shovel grip on the palm of the hand, ii) aligns the wrist in a neutral posture at impact and prevent awkward extension and flexion postures throughout the tree planting task, and iii) provides a carrying mechanism so that tree planters do not have to continuously grip the shovel throughout the course of the day.

According to various embodiments of the invention, the tool receiving surface may have various sizes, shapes and orientations to accommodate a variety of different handles therein to distribute force or impacts from the handle normally directed only into the palm of the hand across a larger area along the inner forearm of the user. Examples include various tool handles, as well as handles of a bicycle directing force into the palms of the user, or other handles found on a variety of occupational equipment or sporting equipment for example.

According to one embodiment, the device is a rigid member which extends across the bottom of the user's forearm and palm of the hand. This ridged member provides support which extends across the user's wrist joint and acts to distribute the force of impact which comes from a device such as a shovel handle which is held in the cavity of the mechanism (FIGS. 1,2 and 3, portion A). The ridged member (FIGS. 1,2 and 3, portion E) serves to hold the users hand, wrist and forearm in proper position (preventing hyperextension seen in FIG. 5), distribute the force of impact away from the wrist joint and palm of hand.

In addition to holding the wrist in a neutral position and distributing the force of impact, the device allows for the user to securely fasten objects such as shovel handles into the palm of the hand. This prevents users from needing to grip a shovel or similar device for extensive periods of time lessening the chance of injuries to the hand and fingers from over use. The fastening mechanism can be achieved by using a ridged support that is curved to the shape of a handle. A shovel may sit against this ridged support member and be fastened into place using a flexible strap which may be fed through a slotted opening to be retained by friction to hold the strap into place, or alternatively fastened using other known fastening techniques including hook and loop fasteners, snap fasteners, buckles, and couplings of various configurations for example. The entire device can be held in place on the forearm using a strap or wrap portion about the forearm similar to conventional wrist braces/splints.

Preferably the palm portion is oriented so as to be substantially coplanar with the arm portion of the splint member. Substantially coplanar is understood herein to include the palm portion lying at a slope of less than 30 degrees from the longitudinal direction of the arm portion. More preferably, the palm portion is either: i) oriented parallel and coplanar to the arm portion, ii) oriented to extend outwardly in a direction of extension at a slope of less than 25 degrees relative to a neutral plane of the arm portion, or iii) oriented to extend inwardly in a direction of flexion relative to a neutral plane of the arm portion so as to prevent extension of the palm of the user relative to the inner forearm of the user.

The tool receiving surface may remain open for ease of insertion and removal of a tool handle into the receiving surface.

Alternatively, the device may further include a strap member configured to secure the tool handle against the lower tool receiving surface. The strap member is preferably operable between an open condition in which the strap member is insertable through a closed loop handle and a closed condition in which the closed loop handle is retained against the lower tool receiving surface. A fastening mechanism may be further provided which is configured to secure the strap member in the closed condition.

The tool receiving surface is preferably generally concave about a tool handle axis. The tool axis in some embodiments is oriented perpendicularly to the longitudinal direction of the arm portion substantially parallel to a neutral plane of the arm portion. Alternatively, the tool handle axis may be oriented transversely and non-perpendicularly to the longitudinal direction of the arm portion substantially parallel to a neutral plane of the arm portion. In yet further embodiments, the tool receiving surface may be angularly adjustable relative to the arm portion such that an orientation of the tool handle axis is adjustable relative to the longitudinal direction of the arm portion substantially parallel to a neutral plane of the arm portion.

The device may include an auxiliary support member protruding in a direction of flexion from a neutral plane of the arm portion opposite from the palm supporting surface and proximate to the lower tool receiving surface in which the tool receiving surface and the auxiliary support member collectively define a partially cylindrical surface extending about a tool handle axis for receiving a tool handle therein which is substantially parallel to the neutral plane of the arm portion.

The partially cylindrical surface preferably extends less than 180 degrees about the tool handle axis to allow ready access of a handle into the handle receiving cavity; however, in further embodiments, the partially cylindrical surface may extend about a larger range of degrees, for example 270 degrees, by forming part of the surface such as the finger portion to be flexible.

When a strap member is provided, the strap member may be securable between a free end of the palm portion opposite the arm portion and a free end of the auxiliary support member opposite the palm portion so as to be configured to secure the tool handle against the lower tool receiving surface.

The splint member may further include a finger portion extending in the longitudinal direction from the palm portion opposite from the arm portion in which the finger portion has a finger supporting surface which is convex such that a free end of the finger portion protrudes in a direction of flexion from a neutral plane of the arm portion opposite to the palm supporting surface.

The finger portion may be more flexible than the palm portion to allow the finger portion to be circumferentially clamped about a tool handle by a clamping force applied by the fingers of the user.

A resilient padding member may be supported on the splint member in proximity to the arm supporting surface for engagement against the inner forearm of user. Preferably, the resilient padding member is supported in proximity to a junction of the arm portion and the palm portion for alignment with a wrist of the user in which the padding member has an ergonomic profile for engagement along a portion of arm of the user.

The device is particularly suited for use with a work tool comprising a shaft extending in a longitudinal direction between a first end and a second end, a handle supported perpendicularly to the shaft at the first end of the shaft, and a tool head supported on the shaft at the second end of the shaft which is configured for being impacted in the longitudinal direction of the shaft, wherein the lower tool receiving surface of the wrist brace device receives the handle of the work tool therein.

Various embodiments of the invention will now be described in conjunction with the accompanying drawings in which:

BRIEF DESCRIPTION OF THE DRAWINGS

In the drawings like characters of reference indicate corresponding parts in the different figures.

DETAILED DESCRIPTION

Figure 1:
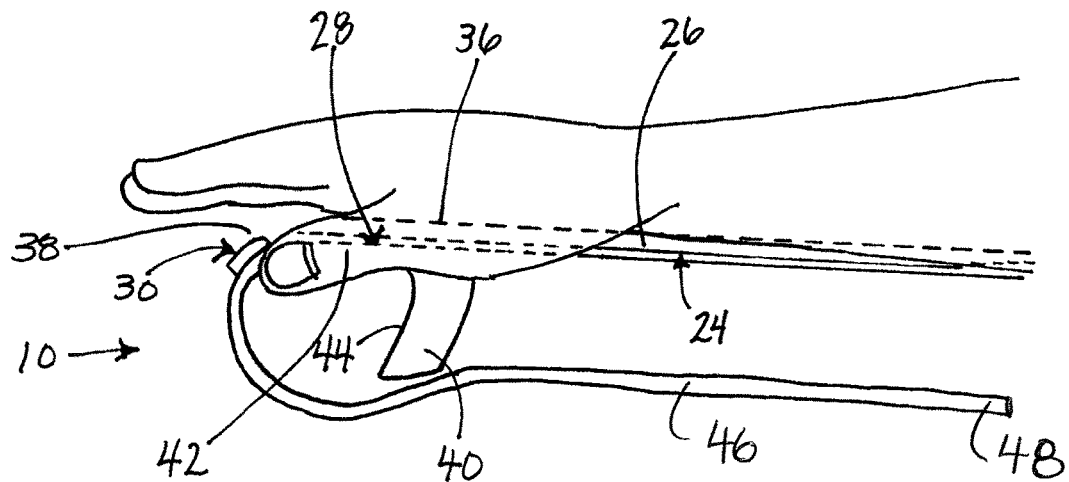
FIG. 1 is a side elevational view of the wrist brace device supported alongside the arm of a user.
Figure 2:
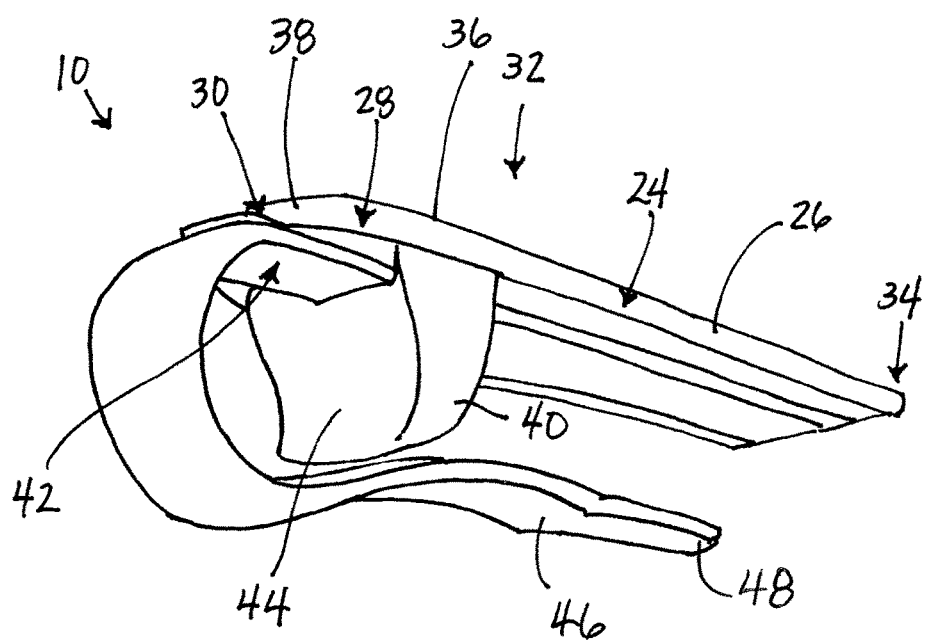
FIG. 2 is a perspective view of the wrist brace device.
Figure 3:
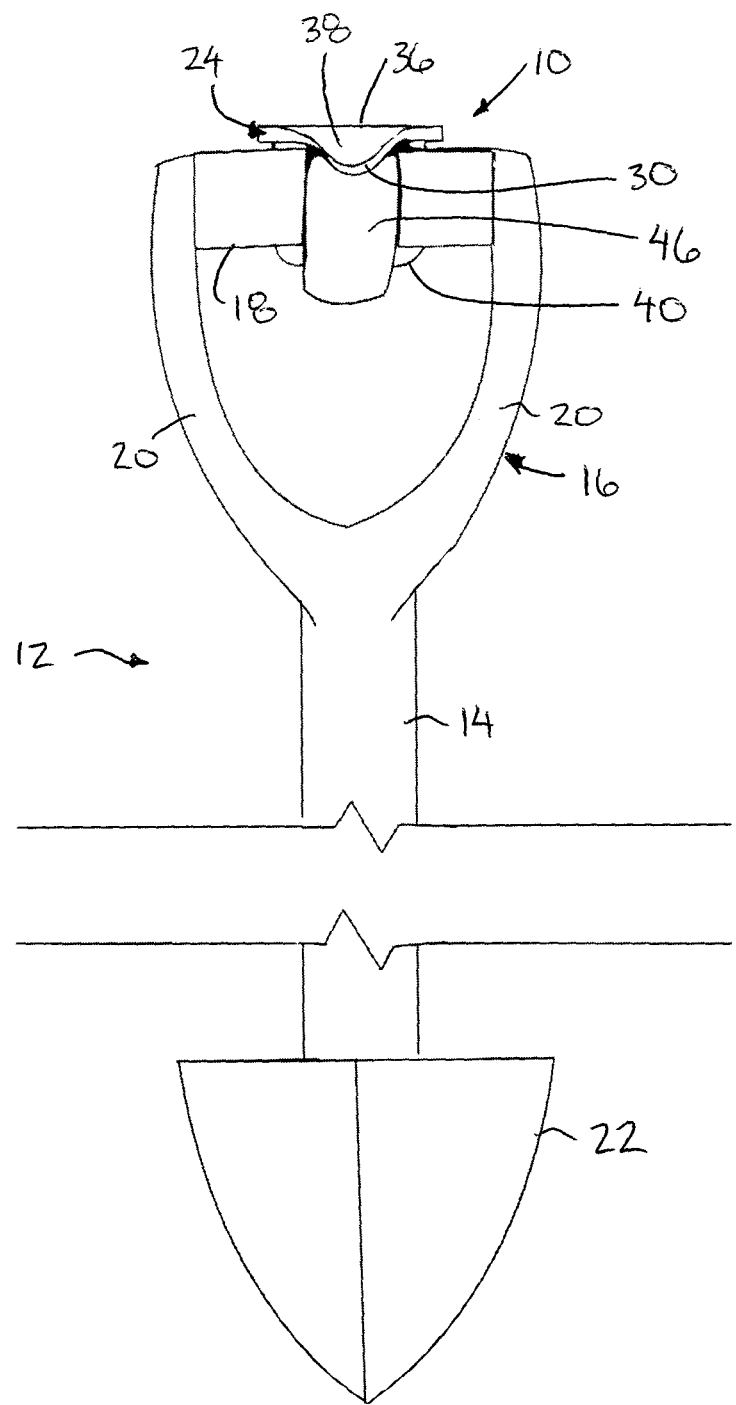
FIG. 3 is an end view of the wrist brace device supporting a tool handle therein.

Referring to the accompanying figures, there is illustrated a wrist brace device generally indicated by reference numeral 10. The device 10 is particularly suited for use with an object having a grip handle, for example various manual labor tools including a shovel 12 and the like, various occupational tools used in the workplace, or various types of sporting equipment such as a bicycle for example.

In the illustrated embodiments, the wrist brace device is shown in use with a shovel 12 of the type having an elongate shaft 14 extending in a longitudinal direction between a first end and an opposing second end. A D-shaped handle 16 is mounted at the first end. The handle 16 includes a handle member 18 arranged to be gripped in the hand of a user which is oriented perpendicularly to the longitudinal direction of the shaft at a location spaced outwardly from the end of the shaft. Two side portions 20 which are curved connect between the end of the shaft and respective opposing ends of the handle member 18 such that the two side portions 20 and the handle member 18 collectively define the D-shape of the handle. In this manner, the handle 16 of the shovel forms a closed loop.

A shovel blade 22 is mounted at the opposing second end of the shaft 14 in the form of a spade blade which tapers to a pointed apex opposite the shaft. The body of the blade spans generally in the longitudinal direction of the shaft. In use, when the shovel is planted into the ground, the resulting impact from the ground onto the shovel is oriented in the longitudinal direction of the shaft, so as to be perpendicular to the handle member 18 gripped in the hand of the user.

Although various embodiments of the wrist brace device 10 are described and illustrated herein, the common features of the various embodiments will first be described. The device 10 includes a rigid splint member 24 which is formed as a single unitary body including an arm portion 26, a palm portion 28, and a finger portion 30 as described in further detail below. At least the arm portion and the palm portion are rigid and fixed in orientation relative to one another in use.

The arm portion 26 generally comprises a flat plate which is elongate in a longitudinal direction between a first end 32 and a second end 34 which defines a neutral plane of support for the arm and wrist of the user. The arm portion is intended to be secured along the inner side of the forearm of the user so as to span a portion of the forearm and the wrist of the user in a working position.

The palm portion 28 extends away from the first end of the arm portion in the longitudinal direction of the arm portion. The palm portion includes an upper palm supporting surface 36 which is substantially coplanar with a corresponding arm supportive surface along the side of the arm portion 26. In this manner, when the palm of the user is supported against the upper palm supporting surface of the palm portion 28, the palm of the user is substantially or primarily coplanar with the forearm of the user in a neutral position of the wrist. The upper palm supporting surface is a generally flat plate-like surface in the illustrated embodiment, however alternative ergonomic shapes may be employed provided that the palm supported thereon remains oriented primarily in a coplanar relationship with the longitudinal direction of the forearm of the user. Substantially or primarily coplanar with the forearm is understood herein to define that the palm of the user is nearer to a co-planar relationship with the forearm than perpendicular to the longitudinal direction of the forearm.

The finger portion 30 extends longitudinally from the end of the palm portion 28 opposite from the arm portion for engaging the knuckles and a portion of the fingers of the user thereon. The finger portion has a convex upper surface 38 upon which the portion of the fingers of the user are engaged in the working position. The finger portion curves or projects away from the plane of the palm portion and the arm portion of the splint member in a direction opposite or away from the palm supporting surface 36, that is in a direction of flexion of the wrist of the user relative to the neutral plane of the arm portion. In this manner the finger portion curves downwardly when the upper palm supporting surface is oriented to face upwardly. The finger portion 30 is formed to be more flexible than the remainder of the splint member (including the palm portion and the arm portion) so as to enable the finger portion to be clamped about a tool handle by a clamping force applied by the fingers of the user to constrict a radius of curvature of the tool receiving surface and clamp the tool receiving surface in a circumferential direction about the tool handle.

The rigid splint member 24 further includes an auxiliary support member 40 integrally formed as a rigid unitary body with the splint member to project generally perpendicularly outwardly from the plane of the arm portion and the palm portion in a downward direction opposite to the upper palm supporting surface when the palm supporting surface is oriented to face upwardly. The support member 40 extends outwardly from the palm portion of the splint member, in a direction of flexion of the wrist of the user relative to the neutral plane of the arm portion, directly opposite the palm supporting surface with a portion of the palm portion and finger portion protruding in the longitudinal direction beyond the auxiliary support member. A resulting tool receiving cavity is defined between the auxiliary support member 40 and the free end of the finger portion in the longitudinal direction which includes a tool receiving surface 42 on the underside of the splint member which is generally parallel or coplanar to the arm portion while being oriented to face downwardly in the opposing direction from the upwardly facing palm supporting surface 36.

Figure 4:
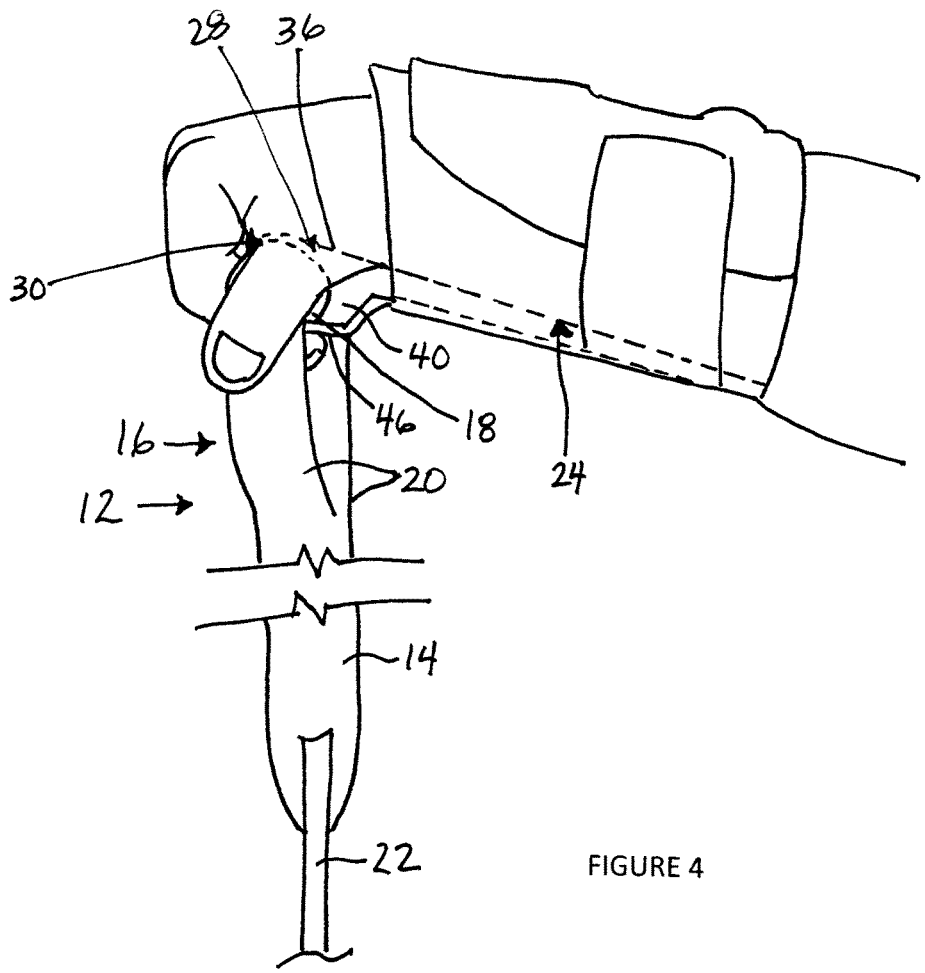
FIG. 4 is a side view of the wrist brace device supported on the arm of the user including a tool received therein.
Figure 5:
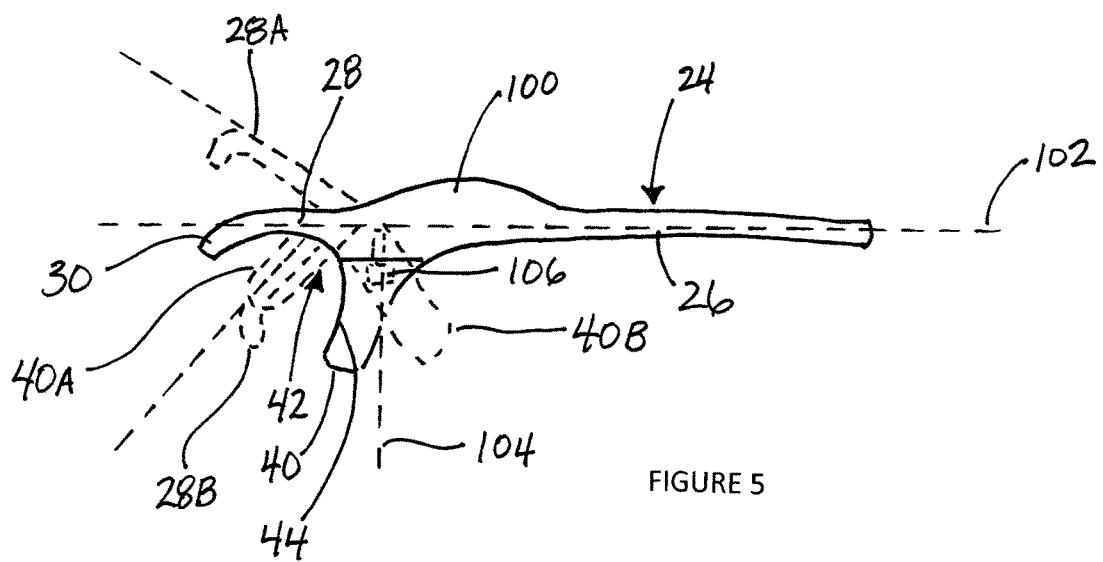
FIG. 5 is a schematic side elevational view of the wrist brace device according to a further embodiment of the present invention in which additional embodiments are shown illustrated in broken line.
Figure 6:
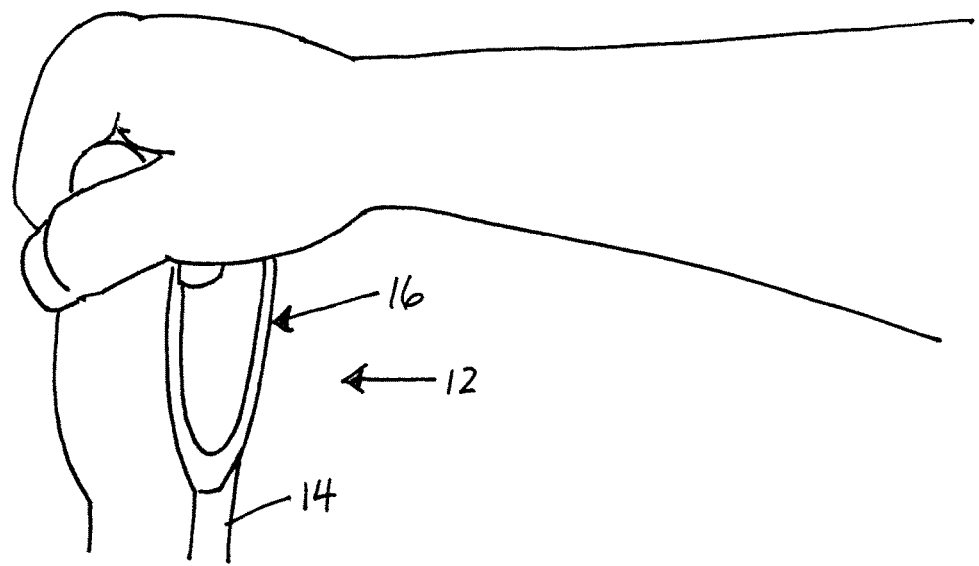
FIG. 6 is a side elevational view of a proper neutral position of the wrist for using a closed loop handled shovel.
Figure 7:
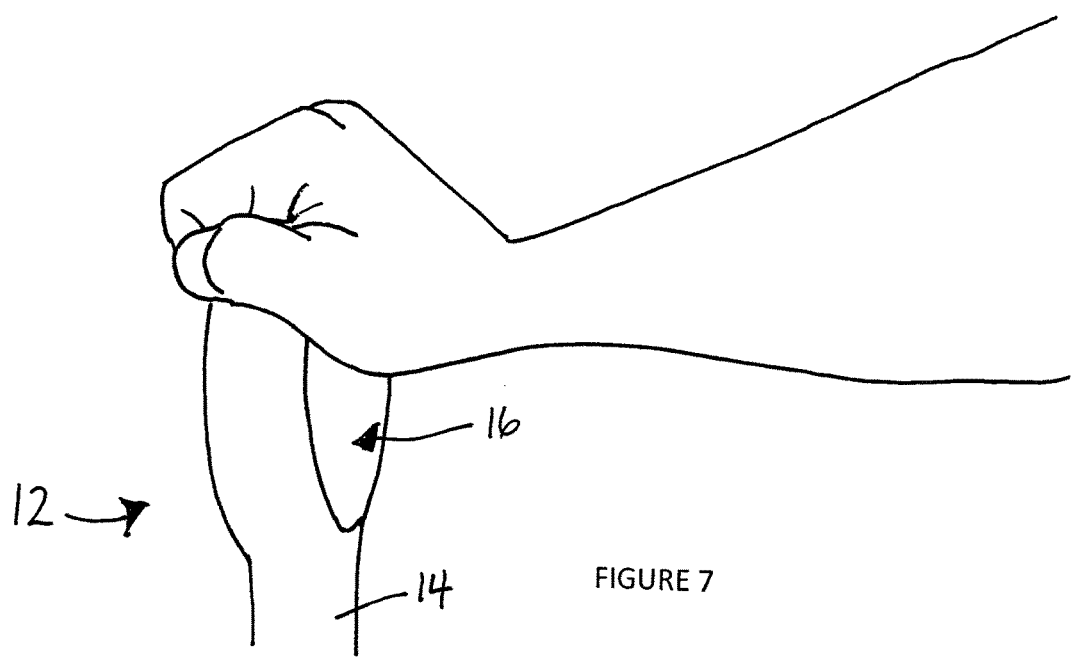
FIG. 7 is a side elevational view of an improper overextended position of the wrist when using a closed loop handled shovel.

As best shown in FIGS. 4 and 5, the auxiliary support member 40 protrudes from the splint member at a location in proximity to a junction between the arm supporting surface of the arm portion 26 and the upper palm supporting surface of the palm portion 28 such that the tool receiving cavity is located directly opposite from the upper palm supporting surface. An inner side 44 of the auxiliary support member 40 which faces the free end of the finger portion 30, as well as the underside of the finger portion 30, are each generally concave such that the underside of the finger portion, the tool receiving surface 42, and the inner side 44 of the auxiliary support member 40 collectively define a partial cylindrical surface about a tool handle axis. The partial cylindrical surface about the tool receiving cavity is suitably sized for receiving the handle member 18 of the tool therein. The partial cylindrical surface extends less than 180 degrees about the resulting tool handle receiving cavity in the illustrated embodiment such that the such that the open side of the cavity readily accepts the handle of the tool therein without any flexing of the rigid components relative to one another being required. As further evidenced in the drawings, the partially cylindrical surface of the tool receiving cavity extends less than 180 degrees about a tool cavity axis of the tool receiving cavity such that the tool receiving cavity remains open at a location which is diametrically opposite from the palm portion relative to the tool cavity axis so as to more readily accept the handle of a tool therein.

In use, the user employs a series of forearm straps or brace structure which extends about the forearm of the user for securely fastening the arm portion of the splint member against the inner side of the forearm and the inner side of the wrist of the user. The splint member is positioned such that the palm of the user is supported against the upper palm supporting surface of the palm portion of the splint member while the palm portion remains substantially coplanar with the longitudinal direction of the forearm. The handle member of the shovel is then inserted into the tool receiving cavity for abutment against the tool receiving surface 42 and the strap member 46 is inserted through the closed loop handle and optionally through the slot in the auxiliary support member 40 to be secured in the closed position with the shovel handle retained against the tool receiving surface 42. The user then orients the shovel for impact into the ground with the shaft of the shovel oriented substantially perpendicularly to the ground and substantially perpendicularly to the common plane of the palm supporting surface and the arm portion of the rigid splint member.

Turning now to the illustrated embodiment of FIGS. 1 through 4, the tool handle axis in this instance is oriented perpendicularly to the longitudinal direction, while being substantially parallel to or substantially coplanar with the plane of the palm supporting surface and the arm portion.

Also as shown in the illustrated embodiment of FIGS. 1 to 4, a strap member 46 is provided in the form of a woven fabric material formed into an elongate strand for selectively securing the tool handle to the device 10. A first end 48 of the strap member is secured along the tool receiving surface 42 and the underside of the finger portion 30. The opposing second end of the strap member is selectively securable relative to the free end of the auxiliary support member 40 opposite from the palm portion 28.

In this manner, the strap member 46 is operable between an open position to accept the tool handle into the cavity and a closed position for retaining the handle therein. In the open condition, the tool receiving cavity remains open for receiving a tool handle therein while the second end of the strap member is free and readily insertable into the closed loop of the tool handle. In the closed condition, the strap member spans between the free end of the finger portion and the free end of the auxiliary support member so as to span the open side of the tool handle receiving cavity and form a closed loop secured about the tool handle. In this manner, the tool handle is retained against the tool receiving surface 42 at the underside of the palm portion of the splint member. In the illustrated embodiment of FIGS. 1 through 4, the strap member is secured to one or both of the outer surface of the auxiliary support member 40, or the outer surface of the arm portion 26 in the closed condition using mating hook and loop fasteners secured to respective ones of the strap member and the splint member.

In further embodiments, additional buckles, clamps or clasps, or fasteners could be employed to provide further resistance to secure the strap member in the closed position more securely. In yet a further arrangement, a slotted opening may be provided at the free end of the auxiliary support member 40 through which the free end of the strap member 40 can be inserted. In this instance, the strap member is preferably frictionally retained within the slotted opening to provide some frictional resistance which at least partially retains the strap member in the closed condition.

Turning now to a further embodiment shown in FIG. 5, the tool receiving surface 42 is shown to remain open such that no strap member is required in this instance. The partially cylindrical surface formed by the tool receiving surface 42 and the inner side 44 of the auxiliary support member 40 remains similar in shape so as to extend less than 180 degrees about a respective tool handle axis, however, the user simply retains the tool handle within the tool receiving cavity with their fingers curled about the handle for clamping the handle upwardly against the tool receiving surface.

The embodiment of FIG. 5 is further distinguished by the addition of a resilient padding member 100 which is supported on the upper arm supporting surface of the arm portion in proximity to the palm portion. More particularly the padding member 100 is ergonomic in profile so as to conform to the profile of the wrist of the user substantially at the junction of the arm portion and the palm portion of the splint member. In addition to the ergonomic profile of the padding member 100, the upper arm supporting surface of the arm portion may also be ergonomic in profile. More particularly the arm portion and/or the palm portion may be slightly curved to have a convex supporting surface engaged against the inner forearm of the user resulting in the palm portion being slightly deflected in a direction of flexion of the wrist of the user relative to a neutral plane 102 of the arm portion and the forearm of the user supported thereon.

In yet further embodiments, as shown in broken line in FIG. 5, the palm portion may be deflected in a direction of extension relative to the neutral plane as shown by the palm portion 28A in broken line. Although an angular deflection in the direction of extension of up to 30° from the neutral plane is envisioned while still being considered substantially coplanar, a deflection of the plane of the palm portion being less than 25, 20, or 15 degrees from the neutral plane of the arm portion may be preferred to prevent an overextension of the wrist joint of the user in response to tool impact forces applied to the tool receiving surface of the palm portion in use.

Alternatively, the palm portion may also be deflected in a direction of flexion relative to the neutral plane of the arm portion as shown by the palm portion 28B in broken line. An angular deflection in the direction of flexion of 30° from the neutral plane or less is preferred to maintain the palm portion substantially coplanar with the plane of the arm portion and maintain the wrist of the user in a substantially neutral position.

In either instance, when the palm portion is not co-planar with the arm portion, the auxiliary support member 40 remains oriented in rigid relation to the palm portion so as to define a handle receiving cavity formed by the tool receiving surface 42 and the inner side 44 of the auxiliary support member 40 which is sized and shaped to receive a handle therein. The auxiliary support member 40 is accordingly angular offset from a perpendicular relationship to the arm portion when the palm portion is angularly offset from an exactly co-planar relationship with the arm portion as shown in broken line by reference characters 40A and 40B respectively. Regardless of the orientation of the palm portion to be offset in the direction of flexion, to be offset in the direction of extension, or to be coplanar with the neutral plane of the arm portion, a plane of the upper palm supporting surface of the palm portion (represented in broken line in FIG. 5) intersects the neutral plane 102 of the arm supporting surface at a junction between the arm portion and the palm portion at an angle between the plane of the palm portion and the neutral plane of the arm portion of between 0 and 30 degrees as described above.

In yet further embodiments, the tool handle axis of the partially cylindrical surface defined by the tool receiving surface 42 and the inner side 44 of the auxiliary support member 40 may be oriented non-perpendicularly to the longitudinal direction of the arm portion while still being generally transverse to the longitudinal direction and while also still be substantially parallel to the neutral plane 102 of the arm portion. For example, of the tool handle axis may be offset in either direction from the neutral plane by approximately 30° from a central orientation oriented perpendicularly to the longitudinal direction. Typically, the tool handle axis remains substantially parallel to the neutral plane of the arm portion throughout the different angular orientations relative to the longitudinal axis.

In some instances, the auxiliary support member 40 is supported relative to the remainder of the splint member to be rotatable about an adjustment axis 104 which is oriented generally perpendicularly to the neutral plane of the arm portion. A suitable set screw 106 may define the axis of rotation of the auxiliary support member 40 relative to the remainder of the splint while also enabling the screw to be tightened for locking the orientation of the auxiliary support member 40 relative to the splint member at a selected orientation in use.

In yet further embodiments, any of the variations to the wrist brace device 10 as described in FIG. 5 may be combined with a strap member according to the first embodiment, or any other additional features of the first embodiment.

Although the illustrated embodiments are described in relation to the handle of a shovel, in further embodiments the overall shape, orientation and size of the handle receiving cavity may be varied so as to be more compatible with other types of handles.

Since various modifications can be made in my invention as herein above described, it is intended that all matter contained in the accompanying specification shall be interpreted as illustrative only and not in a limiting sense.

The invention claimed is:

1. A wrist brace device comprising:
a splint member including an arm portion and a palm portion which are rigid and fixed relative to one another;
the arm portion having an arm supporting surface extending in a longitudinal direction for extending longitudinally along a portion of an inner forearm of a user for securement in relation to the inner forearm of the user;
the palm portion having an upper palm supporting surface and a lower tool receiving surface opposite from the upper palm supporting surface;
the upper palm supporting surface extending from the arm portion in the longitudinal direction of the arm portion such that the palm portion is configured to support a palm of the user thereon to extend in a direction of the inner forearm of the user;
the lower tool receiving surface being configured to receive a tool handle thereon substantially in alignment with the palm of the user; and
a strap member configured to secure the tool handle against the lower tool receiving surface.

2. The device according to claim 1 wherein the palm portion is oriented so as to be substantially coplanar with the arm portion of the splint member.

3. The device according to claim 1 wherein the palm portion lies at a slope of less than 30 degrees from the longitudinal direction of the arm portion.

4. The device according to claim 3 wherein the palm portion is oriented to extend outwardly in a direction of extension at a slope of less than 25 degrees relative to a neutral plane of the arm portion.

5. The device according to claim 3 wherein the palm portion is oriented to extend inwardly in a direction of flexion relative to a neutral plane of the arm portion so as to prevent extension of the palm of the user relative to the inner forearm of the user.

6. The device according to claim 1 wherein the strap member is operable between an open condition in which the strap member is insertable through a closed loop handle and a closed condition in which the closed loop handle is retained against the lower tool receiving surface.

7. The device according to claim 6 further comprising a fastening mechanism configured to secure the strap member in the closed condition.

8. The device according to claim 1 wherein the tool receiving surface is generally concave about a tool handle axis which is oriented perpendicularly to the longitudinal direction of the arm portion substantially parallel to a neutral plane of the arm portion.

9. The device according to claim 1 wherein the tool receiving surface is generally concave about a tool handle axis which is oriented transversely and non-perpendicularly to the longitudinal direction of the arm portion substantially parallel to a neutral plane of the arm portion.

10. The device according to claim 1 wherein the tool receiving surface is generally concave about a tool handle axis and wherein the tool receiving surface is angularly adjustable relative to the arm portion such that an orientation of the tool handle axis is adjustable relative to the longitudinal direction of the arm portion substantially parallel to a neutral plane of the arm portion.

11. The device according to claim 1 further comprising an auxiliary support member protruding in a direction of flexion from a neutral plane of the arm portion opposite from the palm supporting surface and proximate to the lower tool receiving surface, the tool receiving surface and the auxiliary support member collectively defining a partially cylindrical surface extending about a tool handle axis for receiving a tool handle therein which is substantially parallel to the neutral plane of the arm portion, wherein the partially cylindrical surface extends less than 180 degrees about the tool handle axis.

12. The device according to claim 1 further comprising an auxiliary support member protruding in a direction of flexion from a neutral plane of the arm portion opposite from the palm supporting surface and proximate to the lower tool receiving surface, the strap member being securable between a free end of the palm portion opposite the arm portion and a free end of the auxiliary support member opposite the palm portion so as to be configured to secure the tool handle against the lower tool receiving surface.

13. The device according to claim 1 further comprising a finger portion extending in the longitudinal direction from the palm portion opposite from the arm portion, the finger portion having a finger supporting surface which is convex such that a free end of the finger portion protrudes in a direction of flexion from a plane of the arm portion opposite to the palm supporting surface.

14. The device according to claim 13 wherein the finger portion is more flexible than the palm portion.

15. The device according to claim 1 further comprising a resilient padding member supported on the splint member in proximity to the arm supporting surface for engagement against the inner forearm of user.

16. The device according to claim 15 wherein the resilient padding member is supported in proximity to a junction of the arm portion and the palm portion for alignment with a wrist of the user.

17. The device according to claim 1 in combination with a work tool comprising a shaft extending in a longitudinal direction between a first end and a second end, a handle supported perpendicularly to the shaft at the first end of the shaft, and a tool head supported on the shaft at the second end of the shaft which is configured for being impacted in the longitudinal direction of the shaft, wherein the lower tool receiving surface receives the handle of the work tool therein.

18. A method of supporting a work tool comprising a shaft extending in a longitudinal direction between a first end and a second end, a tool handle supported perpendicularly to the shaft at the first end of the shaft, and a tool head supported on the shaft at the second end of the shaft which is configured for being impacted in the longitudinal direction of the shaft, wherein the method comprises:
  providing a splint member including i) an arm portion, ii) a palm portion that is rigid and fixed relative to the arm portion which has an upper palm supporting surface extending from the arm portion in the longitudinal direction of the arm portion, iii) a lower tool receiving surface opposite from the upper palm supporting surface, and vi) a strap member configured to secure the tool handle against the lower tool receiving surface;
  supporting the rigid splint member such that the arm portion extends longitudinally along a portion of an inner forearm of a user and such that the palm portion supports a palm of the user thereon to extend in the longitudinal direction of the arm portion that extends along the inner forearm of the user;
  engaging the handle against the lower tool receiving surface such that the tool handle is in alignment with the palm of the user and such that impacts from the tool head are directed substantially perpendicularly to the upper palm supporting surface and the palm of the user supported thereon; and
  securing the tool handle against the lower tool receiving surface using the strap member.

19. A wrist brace device comprising:
  a splint member including an arm portion and a palm portion which are rigid and fixed relative to one another;
  the arm portion having an arm supporting surface extending in a longitudinal direction for extending longitudinally along a portion of an inner forearm of a user for securement in relation to the inner forearm of the user;
  the palm portion having an upper palm supporting surface and a lower tool receiving surface opposite from the upper palm supporting surface;
  the upper palm supporting surface extending from the arm portion in the longitudinal direction of the arm portion such that the palm portion is configured to support a palm of the user thereon to extend in a direction of the inner forearm of the user;
  a plane of the upper palm supporting surface of the palm portion intersecting a neutral plane of the arm supporting surface of the arm portion at a junction located between the arm portion and the palm portion at an angle of intersection of between 0 and 30 degrees;
  the lower tool receiving surface being configured to receive a tool handle thereon substantially in alignment with the palm of the user;
  an auxiliary support member protruding in a direction of flexion from a neutral plane of the arm portion opposite from the palm supporting surface;
  the auxiliary support member being located in proximity to the junction between arm portion and the palm portion so as to be adjacent to the lower tool receiving surface;
  the tool receiving surface and the auxiliary support member collectively defining a tool receiving cavity for receiving a tool handle therein;
  the tool receiving cavity having a partially cylindrical surface extending about a tool cavity axis of the tool receiving cavity which is substantially parallel to the neutral plane of the arm portion;
  the partially cylindrical surface extending less than 180 degrees about the tool handle axis; and
  the tool receiving cavity being open at a location which is diametrically opposite from the palm portion relative to the tool cavity axis.

* * * * *